Figure 1:
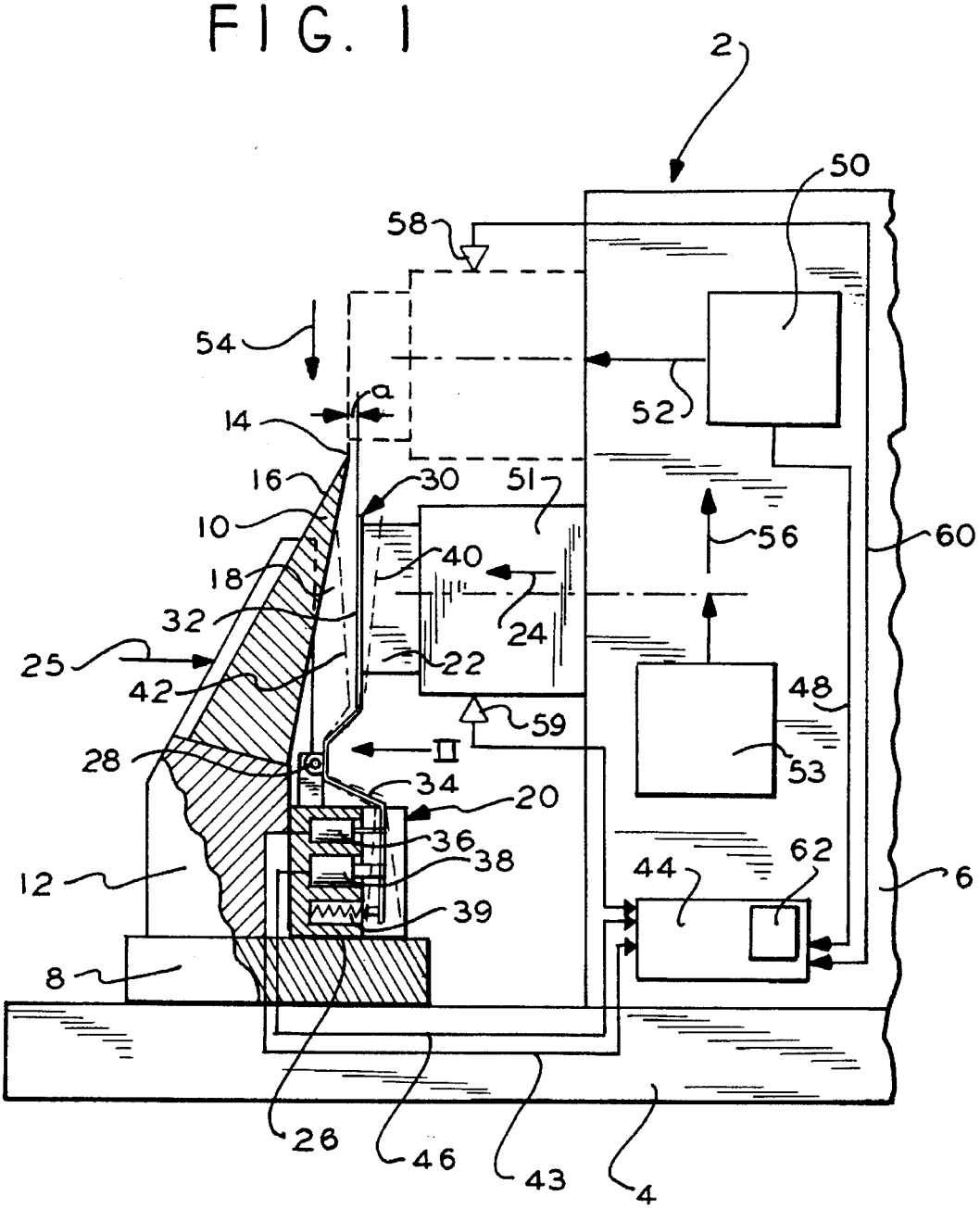

United States Patent [19]

Niesporek et al.

[11] Patent Number: 5,535,654
[45] Date of Patent: Jul. 16, 1996

[54] MICROTOME

[75] Inventors: Christian Niesporek, Wiesloch; Hans Heid, Bammental, both of Germany

[73] Assignee: Microm Laborgerate GmbH, Waldorf, Germany

[21] Appl. No.: 281,430

[22] Filed: Jul. 27, 1994

Related U.S. Application Data

[63] Continuation-in-part of Ser. No. 980,347, Nov. 23, 1992, abandoned.

[30] Foreign Application Priority Data

Nov. 28, 1991 [DE] Germany ............................ 41 39 097.0
Feb. 21, 1992 [DE] Germany ............................ 42 05 256.4

[51] Int. Cl.⁶ .............................. G01N 1/06; B26D 7/06
[52] U.S. Cl. .................. 83/364; 83/367; 83/707; 83/713; 83/915.5; 200/47; 335/276
[58] Field of Search ............................ 83/360, 364, 367, 83/370, 372, 437, 707, 713, 714, 915.5; 200/47; 335/275, 276

[56] References Cited

U.S. PATENT DOCUMENTS

| | | | |
|---|---|---|---|
| 1,732,711 | 10/1929 | Boddie ............................ | 335/276 X |
| 1,753,180 | 4/1930 | Whittingham .................... | 335/276 X |
| 2,209,378 | 7/1940 | Barlow et al. .................... | 200/47 |
| 2,318,359 | 5/1943 | Bellows, Jr. ..................... | 335/276 X |
| 3,055,226 | 9/1962 | Kiessling ........................ | 200/47 X |
| 3,219,770 | 11/1965 | Chasar ........................... | 200/47 |
| 3,293,972 | 12/1966 | Burkhardt et al. ............... | 83/915.5 X |
| 3,418,610 | 12/1968 | Hammond ....................... | 200/47 X |
| 3,667,330 | 6/1972 | Kobernick ....................... | 83/367 X |
| 3,774,130 | 11/1973 | Teichert .......................... | 200/47 X |
| 4,295,017 | 10/1981 | Kashima et al. ................. | 200/47 |
| 4,377,958 | 3/1983 | Leighton ......................... | 83/915.5 X |
| 4,625,608 | 12/1986 | Behme et al. ................... | 83/915.5 X |
| 5,095,792 | 3/1992 | Moody ............................ | 83/372 |
| 5,125,303 | 6/1992 | Hoyland ......................... | 83/360 X |

FOREIGN PATENT DOCUMENTS

| | | | |
|---|---|---|---|
| 1252438 | 12/1960 | France ............................ | 83/364 |
| 1594621 | 9/1990 | U.S.S.R. ......................... | 200/47 |

*Primary Examiner*—Rinaldi I. Rada
*Assistant Examiner*—Clark F. Dexter
*Attorney, Agent, or Firm*—Elliot M. Olstein; Raymond J. Lillie

[57] ABSTRACT

A microtome (2) with a sample holder (51) for a sample (22) to be thinly sectioned and with a knife holder (12) for a cutting knife (10) is described, wherein the sample holder (51), for performing a cutting movement (arrow 54) relative to the knife holder (12), can be driven in a first spatial direction (arrows 54, 56) by means of a first drive device (53), and for performing a coarse adjustment and a section thickness adjusting movement in a second spatial direction (arrow 24) perpendicular to the first spatial direction (54, 56) by means of an electrical second drive device (50). In the vicinity of the cutting knife (10), for defined delimitation of the coarse adjustment movement of the sample holder (51) in the second spatial direction, a delimiting device (20) is provided, which is connected over control means (44), preferably an electronic control, with the electrical second drive device (50).

8 Claims, 2 Drawing Sheets

MICROTOME

This application is a continuation-in-part of application Ser. No. 980,347, filed Nov. 23, 1992, abandoned.

The invention pertains to a microtome with a sample holder for a sample to be thinly sectioned and with a knife holder for a cutting knife displaying a knife blade, wherein the sample holder, in order to perform a cutting movement relative to the knife holder, can be driven by a first drive device in a first spatial direction, and to perform a coarse and a section thickness adjusting movement in a second spatial direction perpendicular to the first spatial direction by means of an electrical second drive device.

Microtomes of this type can be designed as rotary microtomes or slide microtomes. The cutting movement in the first spatial direction can take place via a movement of the sample holder and/or via a movement of the knife holder. In the first drive device for performing the cutting movement and performing a return movement in opposition to the cutting direction, a manually actuable and/or an electric motor-driven drive device may be involved. A rotary microtome of the above-mentioned type is known, for example, from U.S. Pat. No. 4,625,608.

For making thin sections, it is necessary in microtomes of the initially-mentioned type to position the sample holder with the sample to be sectioned with regard to the cutting knife fixed in the knife holder at the beginning of work. This is done by means of a so-called coarse adjustment movement. Especially in the case of microtomes with an electrical drive device instead of a manually actuated drive device, up to now the danger has existed of an uncontrolled contact between the sample to be sectioned, fastened to the sample holder, and the cutting edge of the cutting knife. In this way not only can damage to the cutting edge of the cutting knife and/or damage to the sample to be sectioned take place, but also, damage to the entire microtome.

From U.S. Pat. No. 3,667,330 a microtome is known which is to be provided with end switches for a defined limit to the movement both of the feed movement of samples to be sectioned with regard to the sample holder, and also the movement of the sample holder relative to the cutting knife. The end switch provided for limiting the movement of the sample holder relative to the cutting knife in this known microtome is arranged on a base plate of the microtome. If samples to be sectioned with different dimensions in the second spatial direction are arranged in the sample holder, which is normal and customary, these different samples to be sectioned are also not cut uniformly, but instead to different thicknesses, which represents a considerable deficiency.

The invention has as its object the creation of a microtome of the initially-mentioned type, in which the above-described deficiencies are eliminated, wherein at the beginning of each operation for sectioning a corresponding sample, the approximation between the sample to be sectioned and cutting knife can be carried out automatically, independently of the respective dimensions of the sample, without the risk of damaging the cutting knife or the microtome.

In accordance with the invention, this object is accomplished in that in the vicinity of the knife holder or the cutting knife, for defined delimitation of the coarse adjustment movement of the sample to be sectioned taking place in the second spatial direction, a delimiting movement is provided, which is linked over a control means with the electrical second drive device, that the delimiting device has a base on which a release lug is positioned so as to be able to be pivoted between two angle end positions, and is provided for actuating a switching means arranged in the base body, connected to the control means in such a way that the first angular position remote from the cutting knife, by means of a switching means over the control means, the electrical second drive device for driving the sample holder in the second spatial direction is activated, that the release lug is adjusted such that after contact of the release lug with the sample to be sectioned and upon reaching a predetermined angular intermediate position provided between the two angle end positions, in which the release lug is oriented in parallel to a sectional plane defined between the cutting knife of the knife cutter and the sectioning movement, the switching means switches over into a second switching position, in which by means of the control means the second drive device is deactivated, and that the release lug is connected to a first drive means arranged in the base, which interacts with the control means in such a way that the first drive means keeps the release lug in the first angle end position until contact occurs between the sample to be sectioned and the release lug, and in the angular intermediate position the first drive means is deactivated by the switching means over the control means, so that the release lug is adjusted by a second drive element into the second angle end position, in which the release lug is in contact with the back surface of the cutting knife or the knife holder.

The delimiting device in accordance with the invention is thus intended to automatically establish the approximation of the sample holder with the sample to be sectioned fixed to it to the cutting knife fastened to the knife holder and to turn off the electrical second drive device in time and in a precisely-defined way by means of the control means so that damage to the knife cutter of the cutting knife, to the sample to be sectioned fastened into the sample holder, and to the microtome overall are reliably prevented.

Because of the fact that in the microtome in accordance with the invention the delimiting device has a base to which a release lug is pivotally fastened between two angular end positions and is intended for actuating a switching means arranged in the base, which is effectively connected to the control means in such a way that in the first angle end position remote from the cutting knife, by means of the switching means over the control means, the electrical second drive device for driving the sample holder in the second spatial direction is activated, a simple and operationally reliably designed delimiting device is provided.

As a result of the fact that the release lug is connected with a first drive means arranged in the base, which interacts with the control means in such a way that the first drive device keeps the release lug in the first angle end position until contact occurs between the sample to be sectioned and the release lug, and in the intermediate angle position the first drive means is deactivated by the switching means over the control means, so that the release lug is switched by a second drive means into the second angle end position, in which the release lug is in contact with the back of the cutting knife or the knife holder, it is guaranteed that after the coarse adjustment, during the performance of sectioning, no further contact takes place between the sample to be sectioned and the release lug of the delimiting device. In addition, by suitably adjusting the release lug on the back of the cutting knife or in the back of the knife holder, it is possible in a simple way to avoid an undesirable gap between the back of the cutting knife or the back of the knife holder and the release lug.

If the sample to be sectioned has contacted the release lug during the coarse adjusting movement, the release lug is pivoted with the aid of the sample to be sectioned, moving toward it in the second spatial direction, from the first angular end position into the predetermined angular intermediate position, parallel to the sectioning plane, and upon reaching this predetermined angular intermediate position, the electrical second drive means —as mentioned—is deactivated, which means that the adjusting movement is automatically interrupted.

The switching means is preferably formed by an electrical switch. The delimiting device advantageously requires only a very small amount of space if the last-mentioned electrical switch is a conventional electrical microswitch.

The control means in the microtome in accordance with the invention is preferably designed as an electronic control, which in combination with the last-mentioned microswitch has the advantage that the switch can be connected over the electronic control with the drive device, so that the switch can be designed without problems as an electrical microswitch, since it need not directly connect the drive power.

It has also proven advantageous if not only the switch is an electrical microswitch, but also the first drive means is formed by an electromagnet. This electromagnet can be designed as a miniature electromagnet, since in this way also the delimiting device has a very compact structure.

The electronic control is preferably interconnected with a first end switch provided for detecting a reversal of the sectioning movement. This first end switch is preferably arranged such that it is actuated by the sample holder in the reverse position before performing a cutting movement.

The electronic control can also be interconnected with a second end switch designed for detecting a reversal of the sectioning movement. This second end switch is preferably arranged such that it is actuated by the sample holder in the reversing position after performing a sectioning movement.

The delimiting device is advantageously arranged such that it is actuated by the sample to be sectioned in its reverse position before performing a return motion opposite to the cutting motion. The electronic control of the microtome in accordance with the invention is preferably provided with an electronic memory.

If the microtome in accordance with the invention is a rotary microtome, the coarse adjustment of the sample to be sectioned takes place in the lower reversal position of the sample holder, i.e., in the reversal position prior to undergoing a return movement opposite to the sectioning movement. If the delimiting device in this lower position of the sample holder detects the approach of the sample to be sectioned and the delimiting device in the angular intermediate position strikes the electronic control with the corresponding output signal, the coarse adjusting movement in the second spatial direction is interrupted. Then the sample holder can perform a return movement in the first spatial direction with the aid of the first drive device until the sample holder in its upper reversal position actuates the first end switch before performing a sectioning movement.

Figure 2:
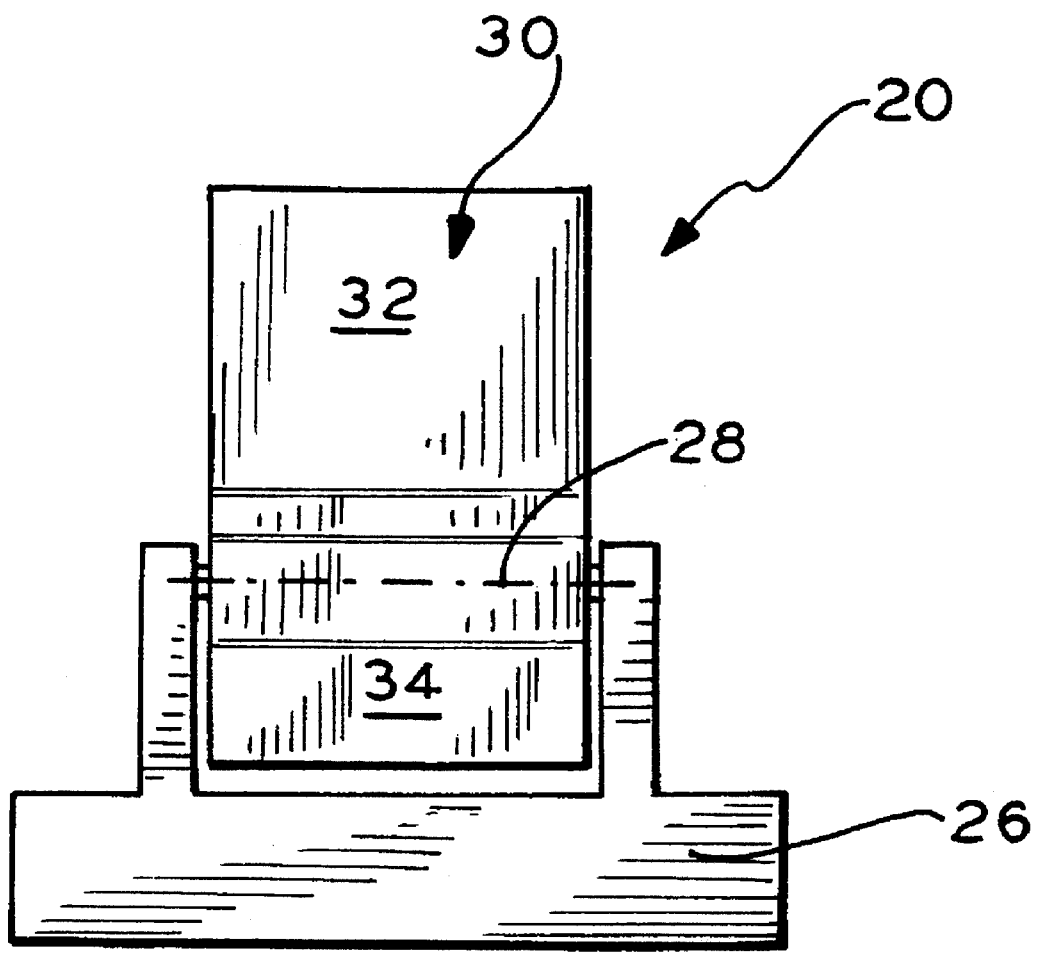

Additional details, features and advantages will be explained in the following on the basis of an exemplified embodiment, shown schematically in the drawing, of the delimiting device in conjunction with a sample to be sectioned, a cutting knife arranged in a knife holder, and additional constituents of the microtome in accordance with the invention. These show:

FIG. 1 A side view of a microtome, cut away and partially shown in sectional view, with a delimiting device for accurately delimiting the coarse position of a sample to be sectioned relative to the cutting knife of the microtome, and FIG. 2 A front view of the delimiting device along the line of arrow II in FIG. 1.

FIG. 1 shows, sectionally and partially cut away, a microtome 2, especially a rotary microtome, with a base 4 and a housing 6 provided on the base 4, and shown in cut-away view. A cutter includes a cutting knife 10 fastened to a knife holder 12. The cutting knife 10 has cutting edge 14, a front surface 16 and a back surface 18. On the knife holder 12 or on a base piece 8 of the microtome 2, in the vicinity of the cutting knife 10 or its back surface 18, a delimiting device 20 is arranged, which is provided for defined delimitation of the positioning movement of a sample 22 to be sectioned. This adjusting movement of the sample 22 is indicated by the arrow 24. Naturally it is also possible not to adjust the sample 22 relative to the cutting knife 10, but instead the cutting knife 10 relative to the sample 22 to be sectioned, as is indicated by the arrow 25.

The delimiting device 20 has a base 26 designed as a housing, on which by means of a pivoting axis 28 a release lug 30 is positioned to be pivotally moveable. The release lug 30 is designed as a two-armed lever, wherein the one lever arm 32 is assigned to the cutting knife 10 or the sample 22 that is to be sectioned, and the second lever arm 34 is assigned to an electrical switch 36, an electromagnet 38, and a spring element 39.

The release lug 30 is pivotable around the pivoting axis 28 between a first angle end position 40 and a second angle end position 42. The first angle end position is indicated in FIG. 1 by a thin broken line and the second angle end position is shown in FIG. 1 by a thin dot and dash line. Between the two angle end positions 40 and 42 there is a defined angle intermediate position, shown in FIG. 1 with solid lines.

The switch 36 and the electromagnet 38 are connected to an electronic control 44, shown schematically as a block, which is indicated by the arrows 43 and 46. The electronic control 44 is connected by a connecting line indicated by an arrow 48 with an electronic drive device 50, which like the electronic control 44 is only shown schematically as a block. The electrical drive device 50 serves to drive a sample holder 51, to which the sample 22 to be sectioned is fixed, in a second spatial direction. This drive in the second spatial direction is indicated by the arrow line 52. With the aid of the electrical drive device 50 a coarse adjusting movement of the sample 22 to be sectioned in the direction of the arrow 24 in the second spatial direction toward the cutting knife 10 takes place, and after this coarse adjustment, in each case a predetermined or preset section thickness fine adjustment in the second spatial direction. The electrical drive device 50 can also be provided for the corresponding coarse adjustment or section thickness fine adjustment of the cutting knife 10 in the second spatial direction relative to the sample 22 to be sectioned, as is indicated by the arrow 25. A sectioning movement taking place in the first spatial direction perpendicular to the second spatial direction, in the direction of the arrow 54, or a restoring or withdrawing movement in the direction of the arrow 56, opposite the cutting direction, can take place by means of a first drive device 53. This can be a manual or an electric motor-driven drive device 53.

A sensor 58 indicated schematically in FIG. 1 by a triangular tip is connected to the electronic control 44, as indicated by the arrow 60. The sensor 58, which may for example involve a photocell barrier or an electrical switch, is arranged on the microtome 2 in such a way that it is activated by the sample holder 51 in its upper reversal position—indicated by thin broken lines—before performing a cutting motion in the direction of the arrow 54.

FIG. 2 shows, in a front view, the release lug 30 with the pivot axis 28, around which the release lug 30 is pivotable relative to the base piece 26 of the delimiting device 20. From this figure also, the two-arm design of the release lug 30 with the first lever arm 32 and the second lever arm 34 is visible. It is advantageous if at least the first lever arm 32 of the release lug 30 which comes into contact with the sample 22 to be sectioned has an area that is at least as large as the cross-sectional surface of the sample to be sectioned, since this guarantees that the section of the surface of the usually uneven front surface of the sample to be sectioned 22 located adjacent to the cutting knife 10 or its cutting edge 14 makes contact with the first lever arm 32 of the release lug 30, and thus in a defined intermediate angular position, brings about the corresponding release of the electronic control 44.

The mode of action of the novel microtome 2 or the delimiting device 20 used there will be described in the following on the basis of a rotary microtome, wherein it is understood that the same arrangement can be provided in the case of a slide microtome.

When setting up a sample 22 for sectioning, a rough positioning of the sample 22 relative to the cutting edge 14 of the cutting knife 10 must first be carried out in the second spatial direction (arrow 24). This coarse adjustment is indicated by the arrow 24. Such a coarse adjustment is necessary, since for the purpose of setting up a sample 22, the sample holder 51 and the cutting knife 10 first are, or will be, at corresponding distances from one another. This distance can be selected arbitrarily, since on one hand different samples 22 to be sectioned can have different raw dimensions, and on the other hand, the cutting knife 10 with its knife holder 12 can be shifted or moved as desired relative to the sample holder 51.

The coarse adjustment is made by means of the electrical second drive device 50, with which either the sample 22 to be sectioned is moved appropriately in the direction of the arrow 24, or the cutting knife 10 is moved in the direction of the arrow 25. This approximation up to now has required appropriate control and attentiveness in order to avoid uncontrolled contact between the sample 22 and the cutting edge 14 of the cutting knife 10. For this purpose the delimiting device 20 is provided, which is located in the vicinity of the back area 18 of the cutting knife 10.

The coarse adjustment of the sample 22 to be sectioned with the aid of the electrical second drive device 50 takes place, relative to the sectional movement indicated by the arrow 54, and based on the return or back stroke movement oriented in the opposite direction, which is indicated by the arrow 56, in the lower reverse position of the sample 22 to be sectioned or the sample holder 51. The lower reverse position can thereby be detected by a sensor 59, which like the sensor 58 is illustrated only by an arrow tip.

During the approach of the sample 22 to be sectioned to the cutting knife 10, the release lug 30 can be found in its first angular end position 40 remote from the cutting knife 10. The first angular end position 40 is brought about by the electromagnet 38, which is appropriately energized for this purpose, to pull on the second lever arm 34. At the same time in this first angle end position 40 with the aid of the second lever arm 34 the electrical switch 36 is actuated, so that the switch 36 releases a corresponding signal to the electronic control 44. By means of this signal, through the electronic control 44, the electrical drive device 50 is activated in such a way that with the aid of the electrical drive device 50 the sample holder 51 with the sample 22 to be sectioned, fixed to it, is moved in the direction of the arrow 24 relative to the cutting knife 10, or the cutting knife 10 is moved in the direction of the arrow 25 relative to the sample 22 to be sectioned. This feed drive takes place until the sample 22 to be sectioned contacts the first lever arm 32 of the release lug 30 and pivots the first lever arm 32 of the release lug 30 around the pivot axis 28 (counterclockwise in FIG. 1) into the angular intermediate position. The delimiting device 20 is adjusted in such a way that on reaching the angular intermediate position, i.e., the precisely perpendicular position of the first lever arm 32, which is established by the cutting edge 14 and the cutting movement (arrow 54), the electrical switch 36 is switched into its second switch position. The angular intermediate position thereby can lie precisely in the plane determined by the cutting edge 14 and the sectioning movement according to arrow 54. However, the angular intermediate position can also be located at a certain distance (see FIG. 1) from the last-mentioned plane and parallel to it.

When the switch 36 is switched into its second switch position, an electrical signal is generated, which over the electronic control 44 turns off the electrical drive device 50, i.e., interrupts the coarse positioning between the sample 22 to be sectioned and the cutting knife 10. Subsequently or simultaneously, the electromagnet 38 is deactivated over the electronic control 44, so that it assumes its opposite position, which is its inactive resting position. Thereby the release lug 30 is further pivoted around the pivot axis 28 by a spring element 39 (counterclockwise in FIG. 1), until its first lever arm 32 is adjacent to the back surface 18 of the cutting knife 10. This corresponds to the second angular end position 42 of the release lug 30. The spring element 39 intended for pivoting the release lug 30 from the angular intermediate position into the second angular end position 42 for example can intervene directly on the second lever arm 34 and/or be provided on the electrical switch 36 and/or on the electromagnet 38. The spring force of the spring element 39 is thereby always smaller than the magnetic force of the electromagnet 38 in the active, i.e., energized state, so that the electromagnet 38 can be effective in the corresponding operational state.

In the second angle end position 42 of the release lug 30 it is guaranteed that during the performance of thin sectioning taking place after the coarse adjustment, no contact occurs between the sample 22 to be sectioned and the release lug 30 of the delimiting device 20.

As soon as the release lug 30 is changed into the second angular end position 42, the sample 22 to be sectioned, after performing the coarse adjustment movement taking place in the direction of the arrow 24, is moved with the aid of the first drive device 53 into its upper position, indicated by the arrow 56. In this upper position the sensor 58 is actuated, so that the electronic control 44 is released such that once again, activation of the electrical second drive device 50 takes place in such a way that a distance resulting from the adjustment of the release lug 30, i.e. the distance of lever arm 32 of release lug 30 in angular intermediate position from the plane defined by the cutting edge 14 of the cutting knife 10 and the cutting direction indicated by the arrow 54 is covered between the sample 22 to be sectioned and the cutting edge 14. This distance a is input or may be input into an electronic memory 62 of the electronic control 44. This input into the memory 62 can take place, for example, by means of the electrical second drive device 50, with the aid of which the sample holder 51 with the sample 22 to be sectioned is brought into a middle height position, i.e., at the level of the cutting edge 14, at a distance from the sensors 58 and 59. This approximation, corresponding to the interval a, is input into the memory 62 of the electronic control unit 44, and stored in the memory 62. Then a corresponding thin section, i.e., a movement of the sample 22 to be sectioned in the first spatial direction indicated by the arrow 54 can take place.

Following the performance of a certain thin section operation, the sample holder 51 is returned to its initial position (opposite the arrow 24 in FIG. 1). Thereby, by means of the electro-magnet 38 displaced in its active operating position, the release lug 30 is returned to its first angle end position 40.

We claim:

1. A microtome comprising:

a sample holder (51) for a sample (22) to be sectioned;

a cutter including a cutting knife and a knife holder (12) holding said cutting knife (10), said cutting knife (10) having a cutting edge (14);

a first drive means (53) for driving said sample holder (51) in a first spatial direction (arrow 54) toward the cutter (10,12) for performing a cutting movement, said cutting edge and said first spatial direction defining a sectioning plane; and a second drive means (50) for driving the sample holder (51) in a second spatial direction (arrow 24) perpendicular to the sectioning plane and toward the cutter (10,12) for performing a coarse adjustment and a section thickness adjusting movement;

said microtome characterized in that in the vicinity of the cutter (10,12), a delimiting means for contacting the sample during the movement of the sample (22) in the second spatial direction is provided for defined delimitation of the coarse adjustment movement, wherein the delimiting means (20) is connected over a control means (44) to the second drive device (50);

said delimiting means (20) having a base (26) on which a release lug (30) is supported pivotally between first and second angular end positions (40, and 42, respectively), and a switching means (36) contained in the base (26), wherein said switching means is connected to the control means (44) and to the release lug such that in the first angle end position (40), a portion of said lug remote from the cutting knife (10) positions the switching means in a first switching position activating the second drive device (50) which drives the sample holder (51) in the second spatial direction (24), resulting in that said release lug (30) is contacted with the sample (22) to be sectioned such that said release lug (30) is displaced to a predetermined angular intermediate position, between the two angle end positions (40,42), in which the release lug (30) is oriented generally parallel to said sectioning plane and said portion of the release lug moves the switching means (36) into a second switching position deactivating the second drive device (50); further, said release lug (30) is connected to a lug drive means (38) for holding said release lug in said first angular end position, wherein said lug drive means is contained in the base (26) and interacts with the control means (44) such that the lug drive means holds the release lug (30) in the first angle end position until contact is effected between the sample (22) to be sectioned and the release lug (30), and when said release lug (30) is moved to the angular intermediate position which moves said switching means to said second switching position, the lug drive means is deactivated by the control means (44); and further, said release lug is connected to the base by a spring element (39) so that, when said lug drive means is deactivated, the release lug (30) is displaced by said spring element (39) into the second angular end position (42) in which the release lug (30) is in contact with a back surface (18) of the cutter (10,12).

2. Microtome in accordance with claim 1, characterized in that the switching means (36) is an electrical switch.

3. Microtome in accordance with claim 1, characterized in that the lug drive means (38) is an electromagnet.

4. Microtome in accordance with claim 1, characterized in that the control means (44) is an electronic control.

5. Microtome in accordance with claim 4, characterized in that the electronic control (44) is connected to at least one sensor means (58,59) for detecting a reversal position of the sample holder.

6. Microtome in accordance with claim 5, characterized in that said reversal position is a position of said sample holder at the beginning of said cutting movement (arrow 54).

7. Microtome in accordance with claim 5, characterized in that said reversal position is a position of said sample holder at the end of said cutting movement (arrow 54).

8. Microtome in accordance with claim 4, characterized in that the electronic control (44) has a memory (62).

* * * * *